(12) United States Patent
Vazquez et al.

(10) Patent No.: US 8,312,841 B2
(45) Date of Patent: Nov. 20, 2012

(54) METHOD FOR MITE PRODUCTION

(75) Inventors: Carmen Arteaga Vazquez, Madrid (ES); Juan Carlos Moreno Segura, Madrid (ES); Fernando Juan Vidales, Madrid (ES); Maria Jose Chamorro Salillas, Madrid (ES)

(73) Assignee: Alk-Abello A/S, Horsholm (DK)

( * ) Notice: Subject to any disclaimer, the term of this patent is extended or adjusted under 35 U.S.C. 154(b) by 146 days.

(21) Appl. No.: 12/594,136

(22) PCT Filed: Mar. 28, 2008

(86) PCT No.: PCT/EP2008/053741
§ 371 (c)(1),
(2), (4) Date: Sep. 30, 2009

(87) PCT Pub. No.: WO2008/119762
PCT Pub. Date: Oct. 9, 2008

(65) Prior Publication Data
US 2010/0024048 A1 Jan. 28, 2010

Related U.S. Application Data

(60) Provisional application No. 60/913,635, filed on Apr. 24, 2007.

(30) Foreign Application Priority Data

Mar. 30, 2007 (EP) .................... 07105358

(51) Int. Cl.
*A01K 67/033* (2006.01)
(52) U.S. Cl. .......................... 119/6.6; 119/6.5
(58) Field of Classification Search ............ 119/6.5, 119/6.6, 6.7, 270; 426/2
See application file for complete search history.

(56) References Cited

U.S. PATENT DOCUMENTS

| | | | | |
|---|---|---|---|---|
| 4,172,336 A * | 10/1979 | Aylor | ......... | 43/55 |
| 4,217,367 A * | 8/1980 | Hawley | ......... | 426/2 |
| 5,799,607 A * | 9/1998 | Greany et al. | ......... | 119/6.5 |
| 5,899,168 A * | 5/1999 | Rojas et al. | ......... | 119/6.5 |
| 6,129,935 A * | 10/2000 | White et al. | ......... | 426/2 |
| 6,293,223 B1 * | 9/2001 | Blossey et al. | ......... | 119/6.5 |
| 6,709,862 B2 * | 3/2004 | Curtis | ......... | 435/325 |
| 7,947,269 B2 * | 5/2011 | Bolckmans et al. | ......... | 424/93.7 |
| 2002/0009803 A1 * | 1/2002 | Vajta | ......... | 435/325 |
| 2003/0059445 A1 | 3/2003 | Andre et al. | | |

FOREIGN PATENT DOCUMENTS

CN 1666604 A 9/2005
(Continued)

OTHER PUBLICATIONS

T.Battard et al—Production and Proteomic Characterization of Pharmaceutical-Grade *Dermatophagoides pteronyssinus* and *Dermatophagoids farinae* Extracts for Allergy Vaccines (Int Arch Allergy Immunol 2006;140:295-305).

(Continued)

*Primary Examiner* — T. Nguyen
(74) *Attorney, Agent, or Firm* — Roberts Mlotkowski Safran & Cole, P.C.

(57) ABSTRACT

A method for culturing and producing mites, such as house dust mites, comprising culturing the mites in a suitable solid growth medium, under suitable conditions and for a suitable period of time in a suitable production room, characterized in that the mites are cultured in medium comprised within a closed bag.

20 Claims, 6 Drawing Sheets

An example of a closed bag with mite media.

FOREIGN PATENT DOCUMENTS

| | | | |
|---|---|---|---|
| EP | 1236394 | B1 | 10/2003 |
| GB | 2168680 | A | 1/1986 |
| GB | 2393890 | B | 8/2004 |
| WO | 2006057552 | A1 | 6/2006 |
| WO | 2008015393 | A3 | 2/2008 |

OTHER PUBLICATIONS

F.C. Yi et al—Culture of *Blomia tropicalis* and IgE Immunoblot Characterization of Its Allergenicity (Asian Pacific J. of Allergy and Immunology (1999) 17: 189-194).

J. Miyamoto et al—A Successful method for Mass Culture of the House Dust Mite *Dermatophagoides pteronyssinus* (Japan, J. Exp. Med. vol. 45, 2. p. 133-138, 1975).

G.W. Wharton—House Dust mites (J. Med Ent. vol. 12, No. 6: 577-621, 1976).

Ivanov and Petrova—Attempt to Cultivate *Dermatophagoides pteronyssinus* Mites (Medisinskaja Parazitologija i Parazitarnye Bolezni, 46-49, 1985) (English Abstract).

Zdarkova E—Mass Rearing of the Predator Cheyletus-Eruditus Acarina Cheyletidae for Biological control of Acarid Mites Infesting Stored Products (Crop Protection, 5(2): 122-124, 1986) (English Abstract).

Nomikou et al—Phytoseiid predators suppress populations of *Bemisia tabaci* on cucumber plants with alternative food (Experimental and Applied Acarology 27(1-2), 57-68), 2002.

Ramakers et al.—Mass Production and Introduction of Amblysieus Mckenziei and A. Cucumeris (Bulletin-SROP 6(3), 203-206), 1982.

Steiner et al.—Biological Studies of the Australian predatory mite *Typhlodromips montdorensis* (Schicha) (Acari: Phytoseiidae), a potential biocontrol agent for western flower thrips, *Frankliniella occidentalis* (Pergande) (Thysanopetera:Thripidae), (Australian Journal of Entomology 42, 124-130), 2003.

International Search report and Written Opinion of the International Searching Authority (PCT/EP2008/053741) mailed—Jul. 11, 2008.

State of Intellectual Property Office of the People's Republic of China, Notification of First Office Action dated Jun. 29, 2011 (English translation).

Van Bronswijk et al., J Allergy, vol. 47, No. 1 Jan. 1971, pp. 31-52.

European Patent Office Communication Application No. 08 718 323.2-1260, dated Apr. 29, 2010.

Database Biosis Biosciences Information Service, Philadelphia, PA, US; Database Accession No. PREV19850077528 1985, Ivanov: "Attempt to Cultivate *Dermatophagoaides pteronyssinus* Mites" XP002444230.

\* cited by examiner

Figure 1:

A 250 ml Erlenmeyer flask

Figure 2

Roux culture bottle with offset neck. Capacity 1000 ml.

Figure 3:

An example of a closed bag with mite media.

Figure 4:
An example of bags piled in a rack.

Figure 5:

An example of an open bag filled with media.

Figure 6:

An example of sealing of a bag.

METHOD FOR MITE PRODUCTION

CROSS-REFERENCE TO RELATED APPLICATIONS

The present Application is a US national phase of PCT/EP2008/053741 filed on Mar. 28, 2008 ("PCT Application"), which claims priority from European Patent Application No. 07105358.1 filed on Mar. 30, 2007 and US Provisional Application No. 60/913,635 filed Apr. 24, 2007 both of which are hereby incorporated by references in their entirety into the present Application.

FIELD OF INVENTION

The present invention relates to a method for culturing and producing mites, such as house dust mites, comprising culturing the mites in a suitable growth medium, under suitable conditions and for a suitable period of time in a suitable production room, characterized in that the mites are cultured in medium comprised within a closed bag.

BACKGROUND

Different species of mites, such as house dust mites, are used to prepare allergenic extracts used in allergy formulations for use, for example, in in vivo or in vitro allergy tests, or in desensitizing preparations given to patients.

These mites include, in particular, mites of the following species: *Dermatophagoides pteronyssinus, Dermatophagoides farinae, Blomia kulagini* or *tropicalis, Pyroglyphus africanus*, and *Euroglyphus maynei*.

Numerous prior art documents describe industrial relevant methods for producing mites. With respect to described improvements of the production of mites the prior art may be said to essentially focus on technical elements such as a new medium, optimal humidity, temperature, etc.

Generally speaking, for industrial relevant large scale production the prior art uses FLASKS or alternatively expressed bottles for culturing/rearing of house dust mites.

EP1236394B1 (Stallergenes corresponding to US2003/0059445A1) describes culturing of house dust mites in bottles (see example 1).

T. Batard et al (Int Arch Allergy Immunol 2006; 140:295-305) describes culturing in plastic flasks (see page 296, column 2).

F. C. Yi et al (Asian Pacific J. of Allergy and Immunology (1999) 17: 189-194) describes culturing of house dust mites in Erlenmeyer flasks (see page 190, mid column).

J. Miyamoto (Japan, J. Exp. Med. Vol, 45, 2. p. 133-138, 1975) describes culturing of house dust mites in Roux bottles (see page 134, column 2).

Figure 1:
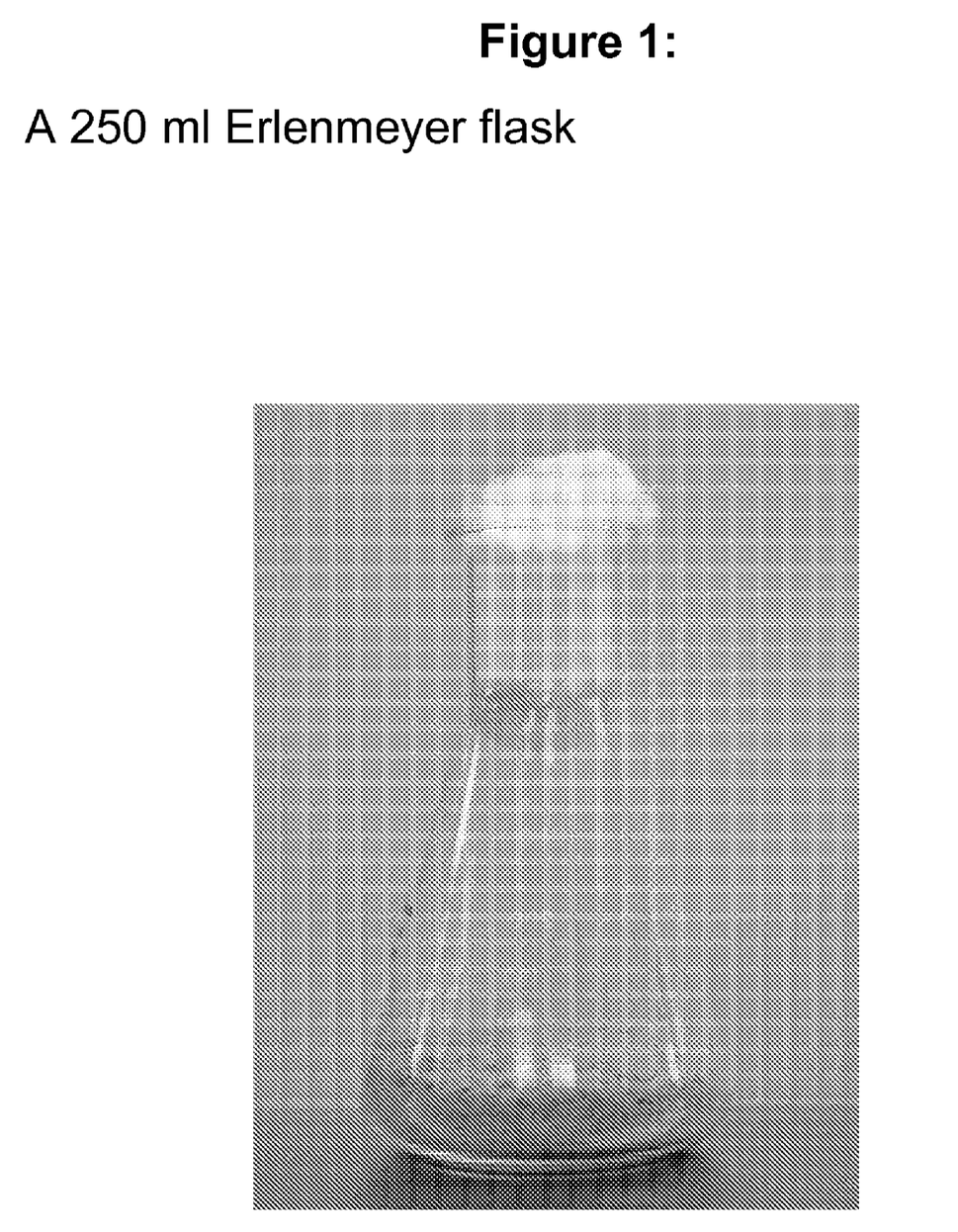
FIG. 1: A 250 ml Erlenmeyer flask.
Figure 2:
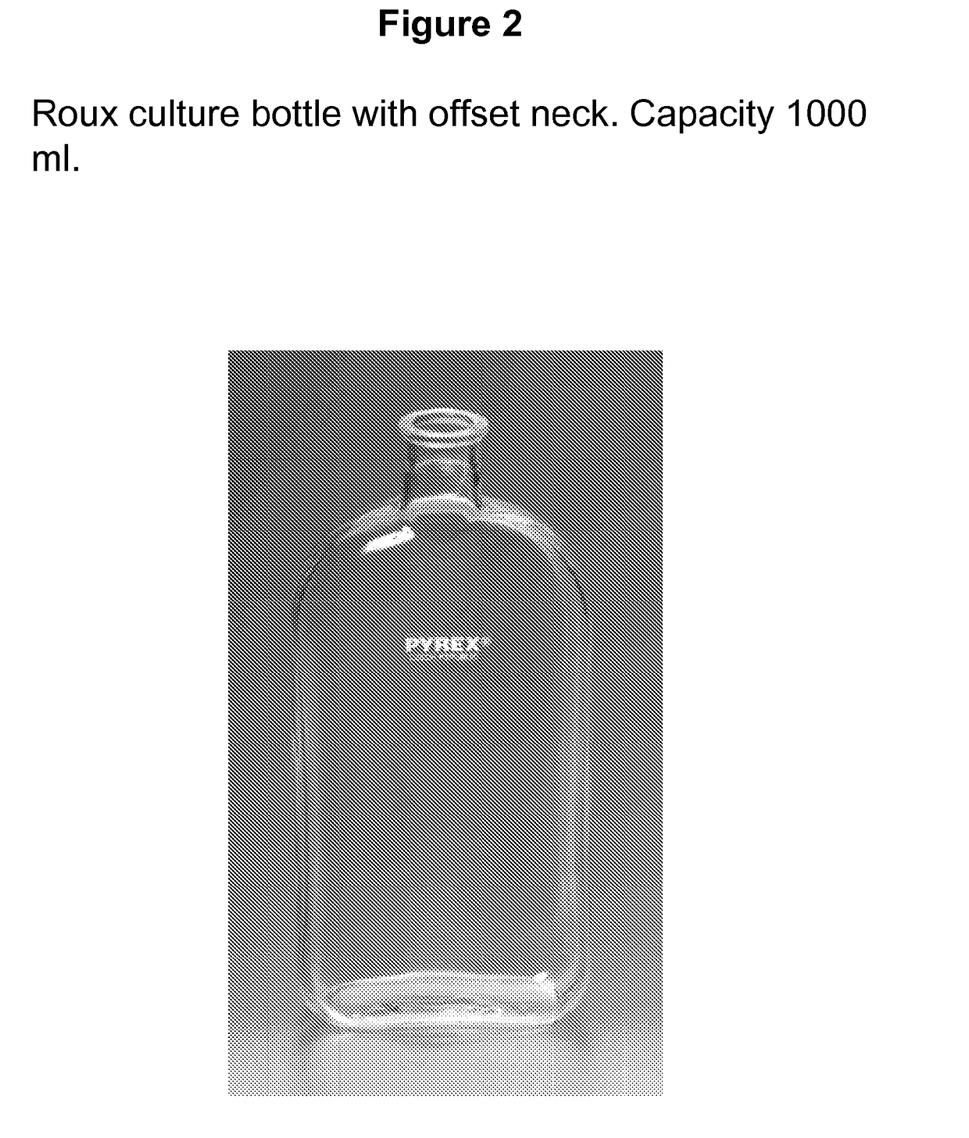
FIG. 2: Roux culture bottle with offset neck. Capacity is 1000 ml.

Culturing of house mites in Erlenmeyer flasks or Roux bottles may be considered as a "standard" procedure of the prior art. A picture of an Erlenmeyer flask is shown in FIG. 1 herein and a picture of a Roux Flask is shown in FIG. 2 herein.

For small scale house dust mite culturing/production the prior also describes use of jars (see e.g. J. Med. Ent. Vol 12, no. 6: 577-621,1976).

Also cultivation of mites in bags/envelopes has been described. Ivanov and Petrova describes in Medisinskaja Parazitoligija i Parazitarnye Bolezni, 46-49, 1985 the small scale production of *Dermatophagoides phteronyssinus* in closed 5×10 cm cellophane bags. According to the authors of the article the danger of mold fungi infections suppressing the mite culture is absent by cultivation of mites in cellophane bags. The amount of growth medium (1 g) and thereby the size of the mite culture that can be obtained in the cellophane bags described in the article is very low. Cellophane is also known to have a very low oxygen permeability and cellophane would therefore not be suitable as a bag material for large scale cultivation of mites.

Other species of mites are used in the field of biological control for reducing pests in crops and in greenhouses.

An article in Crop Protection, 5(2): 122-124, 1986, describes mass rearing of the predator mite *Cheyletus eruditus* to be used for biological control of mites in stored grain or seeds, by a method in which predator mites are cultivated in bags. Square-bottom flour bags of 1 kg capacity was filled with 100 g lettuce seeds, 20.000 prey mites and 100-200 predator mites. Each bag was closed by folding and kept at 25° C. and 75% rh for 28-35 days. To detect the correct time for termination of breeding, the ratio of predator mite to prey mite was checked every second day after day 28.

One important advantage of the cultivation method according to the invention compared to the above method of rearing predator mites is that the bags of the invention comprises a transparent area which allow visual inspection the mite growth in the bag. In general the amount of the cultivation medium used in the method of the invention is also much larger than the amount of the culture medium in the process described above.

GB 2 168 680 describes cultivation of living arthropods or similar predators in envelopes of micro perforated plastic material or paper. The bags described in this application also do not allow optimal inspection of the growth of the mites in the bags because the perforation of the plastic material may disturb inspection of mite growth.

SUMMARY OF THE INVENTION

The problem to be solved by the present invention is to provide an improved method for culturing and producing mites.

Figure 3:
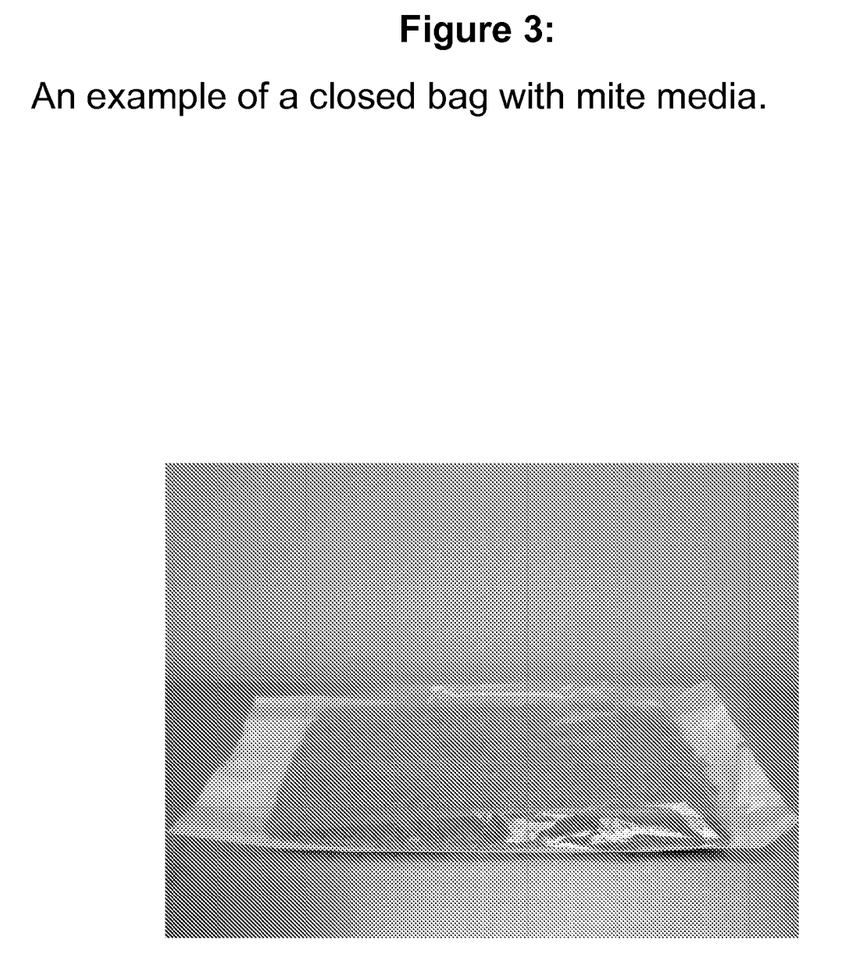
FIG. 3: An example of a closed bag with mite medium as described herein.

The solution is based on the finding that by culturing mites in a suitable bag such an e.g. a paper/plastic bag as shown in FIG. 3 it is possible to significantly improve the production of house dust mites.

The paper/plastic bag as shown in FIG. 3 may be characterized as a bag wherein:
1: one side is made of a cellulose material (e.g. paper) that is oxygen permeable;
2: the other side is made of a transparent plastic material. The plastic may also be oxygen permeable;
3: the size of the bag is roughly 300 mm (broad)×500 mm (length)×with a possibility to be extended to a height of around 65 mm in order for the bag to be able to comprise a relevant amount of mite medium.

As known to the skilled person, a suitable house dust mite growth medium is generally a solid medium since mites are naturally living in beds or other similar places in e.g. a house. Storage mite also feed on solid material and predator mites may feed on prey mites feeding on a solid medium.

Figure 4:
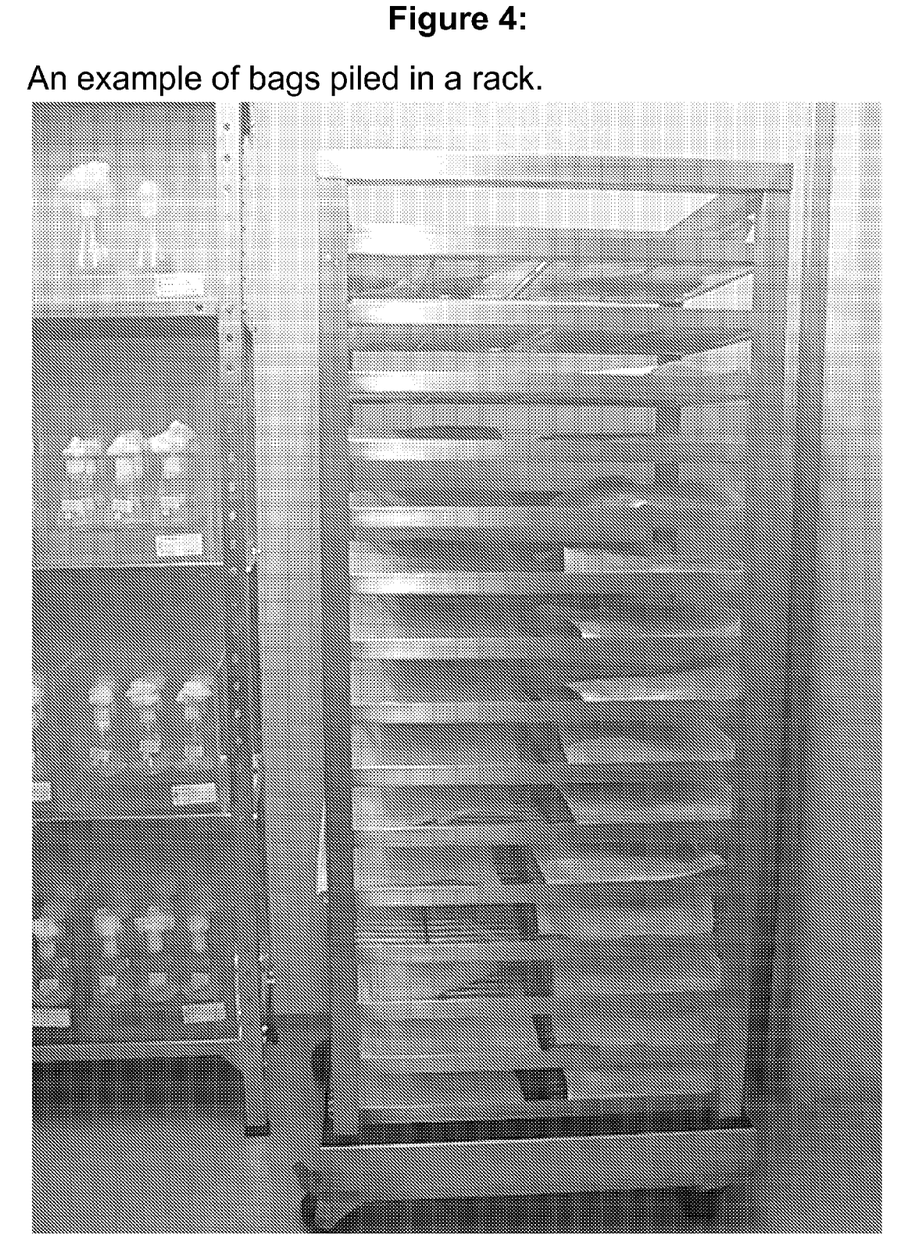
FIG. 4: An example of bags piled in a rack as described herein.
Figure 5:
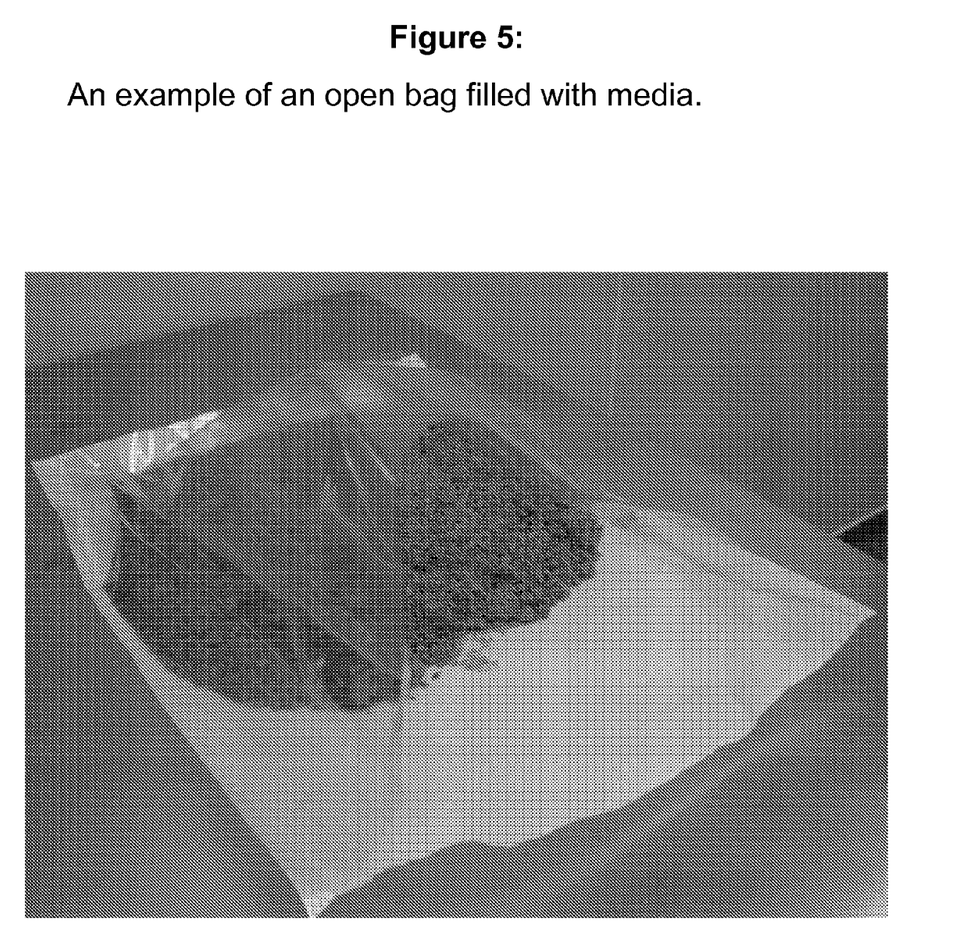
FIG. 5: An example of an open bag filled with medium.
Figure 6:
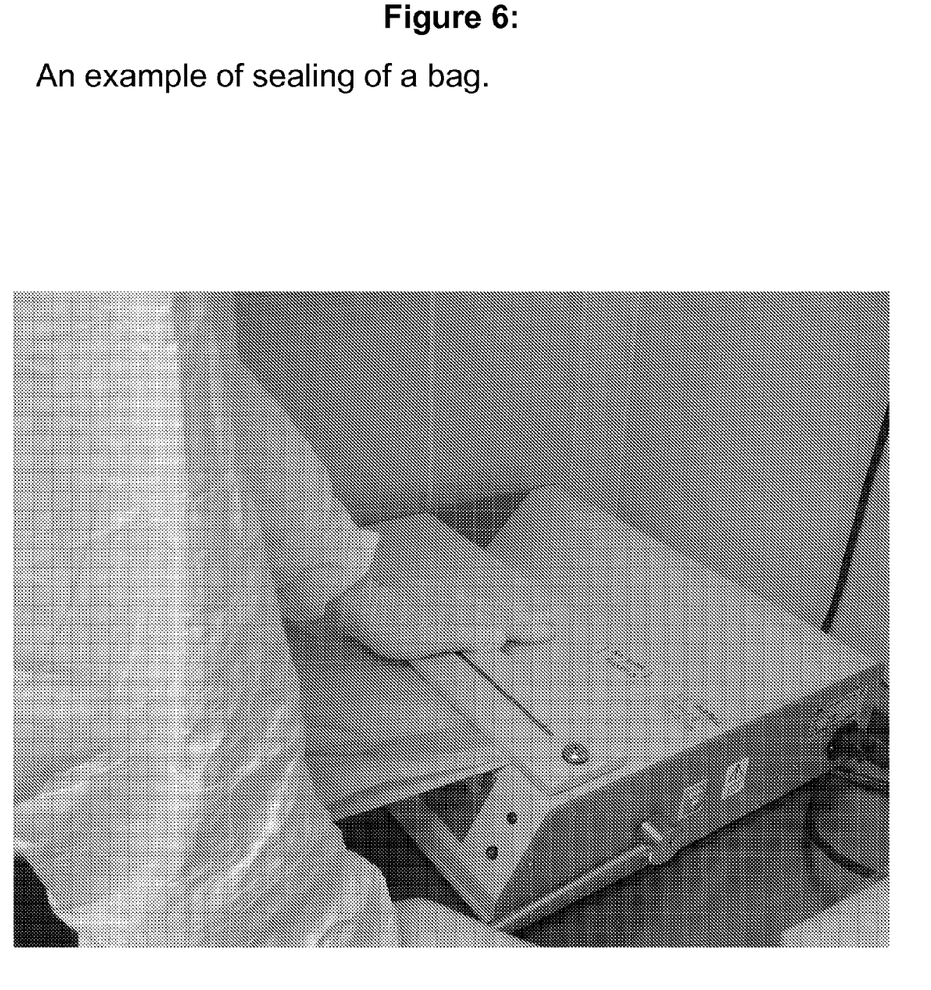
FIG. 6: An example of sealing of a bag.

Advantages of using bags as described herein over prior art uses of flasks (e.g. Erlenmeyer flasks (see FIG. 1) or Roux bottles (see FIG. 2), include:

A: the oxygen permeable (e.g. paper) material on the one side has a surface area that is much bigger than the corresponding "holes" in the top of the prior art flasks. This gives a better and more uniform oxygen supply to the growing mites and therefore a better growth;

B: the improved oxygen supply in the bags also provides the possibility to have more mite culture medium per physical space unit. For instance a 250 ml Erlenmeyer flasks may only comprise around 30-50 g medium (see FIG. 1), whereas the bag shown in FIG. 3 comprises around 500 g medium and may comprise even more (e.g. 1200 g). In the Erlenmeyer flasks a relatively big free space above the medium is needed since the oxygen supply from the relatively small hole in the top of the flask gives a relatively limited oxygen supply;

C: further the mite culture medium may be present as a relatively thin layer in the bags (compare e.g. bag FIG. 3 with Erlenmeyer flasks FIG. 1). This also provides better mite growth since the mites are generally living/growing on the surface (mites are naturally living in beds or other similar "surface" places in e.g. a house);

D: the bags as described herein can relatively easy by piled in e.g. a rack as shown in FIG. 4 and one can consequently have numerous piled bags in a industrial relevant production room (see e.g. FIG. 4). In line of point B above, the end result is that use of the bags significantly increases the production capacity in a room (can contain more mite medium) as compared to use of flasks;

E: the transparent e.g. plastic material allows inspection of the growth directly by e.g. using a stereoscopic microscope without having to take out a sample from the bag. When flasks are used it is much more difficult to use e.g. a stereoscopic microscope and generally a sample has to take out from the flask to analyze the growth status. To take out samples of course implies a risk of contamination;

F: a bag is open at one end and it is therefore easy to put the medium into the bags (see e.g. FIG. 5). This should be seen in comparison with the prior use of flask, where the opening/hole is much smaller. Accordingly, the use of the bags provides the possibility of an automatic (machine not manually) filling of the bags with medium, which make the industrial production more efficient. Once the bag is filled with medium and inoculated with mites the opening of the bag is sealed (se e.g. FIG. 6) before the actual culturing/growth of the mites;

G—The bags allow harvesting of the culture directly in the bags and storage of the material without opening;

H—The bags may be disposable (only one use) making cleaning unnecessary. Also the space used to contain the empty bags is low compared to the space used when Erlenmeyer flasks are used;

I—The weight added because of the container is negligible when bags are used and the danger of breaking the glass during the operations is avoided; and J—The bags can be sealed minimizing the escape of mites and contamination.

As shown in the working examples herein, the use of a bag as described herein for the industrial relevant production of mites provides at least the same yield of mites per g medium as an 250 ml Erlenmeyer flasks that only comprise around 30 g medium (see flask in FIG. 1—a relatively big free space above the medium). One reason for this is the better and more uniform oxygen supply in the bags, which allow efficient growth of the mites in bags with a relatively very little open space around the medium in the bags. As evident from above, this provides the possibility to put in more bags (i.e. more medium) in a production room, as compared to the use of flasks, and therefore much more mites can be produced within the same physical production room.

The skilled person may routinely identify suitable types of bags that may be used to achieve the herein discussed mite production advantages.

Overall a bag that is useful for mite production as described herein may be characterized as a bag that is sufficient oxygen permeable to obtain above mentioned advantages.

A further essential characteristic of the bag is that it comprises an area which is transparent to allow inspection of the mite growth directly e.g. by using a stereoscopic microscope without having to take out a sample from the bag.

Accordingly, a first aspect of the invention relates to a method for culturing and producing mites,
comprising culturing the mites in a suitable solid growth medium, under suitable conditions and for a suitable period of time in a suitable production room,
characterized in that the mites are cultured in a medium comprised within a closed bag, wherein:
  i: the bag has an oxygen permeability that is sufficient to allow growth of the mites;
  ii: the bag comprises an area which is transparent to allow that one can follow the mite growth directly by e.g. using a stereoscopic microscope without having to take out a sample from the bag;
  iii: the culture medium comprising the growing/cultured mites is present as a relatively thin layer within the bag to give a relatively big surface, defined as the culture layer is less than 110 mm in height; and
  iv: the closed bag comprises at least 25 g medium.

The term "culturing" may also be termed "rearing". Both terms may be used interchangeably herein.

Definitions

Prior to a discussion of the detailed embodiments of the invention a definition of specific terms related to the main aspects of the invention is provided.

The term "bag" as used in connection with the novel mite production method as described herein should be understood as the skilled person would understand this term in the present context. The skilled person understands that a bag has a number of characteristics that are different from a flask or a jar. Compared to a flasks or jar a bag is more flexible and may therefore relatively easy change shape (e.g. be folded). In the present context a bag may e.g. be shaped (e.g. folded) around the mite culture medium in order to have relatively little free open space around the medium within the bag (see e.g. FIG. 3 herein). An "open bag" denotes herein a bag with an opening suitable for adding medium into the bag (see illustration in FIG. 5). The opening may be closed (e.g. by heat sealing—see e.g. FIG. 6 herein) in order to have the medium enclosed or contained within the bag during the production. Such a bag is termed a "closed bag".

Embodiments of the present invention are described below, by way of examples only.

DETAILED DESCRIPTION OF PARTICULAR EMBODIMENTS

Oxygen Permeability of the Bag

As said above, the bag has an oxygen permeability that is sufficient to allow growth of the mites. Relevant herein preferred quantitative oxygen permeability parameters are discussed below.

As known to the skilled person, the oxygen permeability of a bag may be seen as related to the porosity of the bag material. According to the art, this may be measured according to the standard ISO 5636-3, Bendtsen method. The standard ISO 5636-3, Bendtsen method is well known to the skilled person.

Measured according to the standard ISO 5636-3, Bendtsen method the bags used in the working examples (illustrated in. FIG. 3) herein has a minimum porosity of 300 ml/min. Said in other words the bags have an air permeability of at least 300 ml/min as measured according to the standard ISO 5636-3, Bendtsen method.

A "normal" paper may have an air permeability of around 10 ml/min. Without being limited to theory is it believed that a bag with an air permeability of at least 5 ml/min has sufficient oxygen permeability to obtain the production advantages as described herein.

Accordingly, in a preferred embodiment the bag is an oxygen permeable bag having an air permeability of at least 5 ml/min as measured according to the standard ISO 5636-3, Bendtsen method. More preferred the bag has an air permeability of at least 50 ml/min as measured according to the standard ISO 5636-3, Bendtsen method, even more preferred the bag has an air permeability of at least 150 ml/min as measured according to the standard ISO 5636-3, Bendtsen method and most preferred the bag has an air permeability of at least 250 ml/min as measured according to the standard ISO 5636-3, Bendtsen method.

Generally speaking, it is believed that for practical purposes it would be difficult to make a suitable bag having an air permeability of more than 20000 ml/min as measured according to the standard ISO 5636-3, Bendtsen method.

As known to the skilled person the standard ISO 5636-3, Bendtsen method is preferably used when the bag comprises cellulose material (e.g. paper).

An alternative herein suitable method for measuring the oxygen permeability of a bag is the known standard test method for oxygen transmission rate through dry packages using a coulometric sensor performed according to the known standard of American Standards National Institute document/ standard ASTM F1307-02.

This ASTM F1307-02 test method covers a procedure for the determination of the steady-state rate of transmission of oxygen gas into packages. More specifically, the method is applicable to packages that in normal use will enclose a dry environment.

A herein suitable apparatus for performing this ASTM F1307-02 test method is a commercial available MOCON® apparatus.

The ASTM F1307-02 test method may be used for virtually any suitable bag material (e.g. paper or plastic) and is therefore the herein most preferred oxygen permeability test method.

The unit of the ASTM F1307-02 test method is $cm^3$ oxygen per bag per day.

Without being limited to theory is it believed that a bag with an air permeability of at least 10 $cm^3$ oxygen per bag per day has sufficient oxygen permeability to obtain the production advantages as described herein.

In a preferred embodiment the bag has an oxygen permeability of at least 10 $cm^3$ oxygen per bag per day measured according to the standard known test method for oxygen transmission rate through dry packages using a coulometric sensor performed according to the known standard of American Standards National Institute document/standard ASTM F1307-02. More preferred the bag has an oxygen permeability of at least 20 $cm^3$ oxygen per bag per day, even more preferred the bag has an oxygen permeability of at least 50 $cm^3$ oxygen per bag per day and most preferred the bag has an oxygen permeability of at least 100 $cm^3$ oxygen per bag per day.

As discussed above, it is demonstrated in working example 1 that by using a bag as described herein (see bag in FIG. 3) for industrial production of mites at least the same yield of mites per g medium as in an 250 ml Erlenmeyer flasks that only comprise around 30 g medium (see flask in FIG. 1—a relatively large free space above the medium) is obtained. One reason for this is the better and more uniform oxygen supply in the bags, which allow efficient growth of the mites in bags despite a relatively very little open space around the medium in the bags. As evident from above, this provides the possibility to have more bags (i.e. more medium- and thereby more mites) in a production room, as compared to the use of flasks, and therefore one can produce much more mites within the same production room.

An alternative way to analyze if a bag has a preferred oxygen permeability is to compare the production of the mites in the bag with the production in a standard 250 ml Erlenmeyer flask that comprise 30 g medium and is closed with a cotton plug (illustrated in flask of FIG. 1).

Accordingly, in a preferred embodiment the bag has an oxygen permeability that is sufficient to provide at least 65% of the yield of mites per g medium in the bag as compared to the yield in an 250 ml Erlenmeyer flask that comprises 30 g medium and is closed with a cotton plug, wherein mites in the bag and the Erlenmeyer flask is cultured under identical conditions, i.e. using the same growth medium, the same growth conditions, the same period of time and the same production room.

More preferred, the bag has an oxygen permeability that is sufficient to provide at least 80% of the yield of mites per g medium in the bag as compared to the yield in an 250 ml Erlenmeyer flask that comprises 30 g medium and is closed with a cotton plug, even more preferred the bag has an oxygen permeability that is sufficient to provide at least 90% of the yield of mites per g medium in the bag as compared to the yield in an 250 ml Erlenmeyer flask that comprises 30 g medium and is closed with a cotton plug and most preferred the bag has an oxygen permeability that is sufficient to provide at least the same yield of mites per g medium in the bag as compared to the yield in an 250 ml Erlenmeyer flask that comprises 30 g medium and is closed with a cotton plug, wherein the bag and the Erlenmeyer flask is cultured under identical conditions, i.e. using the same growth medium, the same growth conditions, the same period of time and the same production room.

Bag Materials and Other Bag Characteristic

Many different suitable bag materials could be used to provide a bag with the herein relevant oxygen permeability.

In a preferred embodiment the bag is a bag made of at least one material selected from the group of materials consisting of a cellulose material (e.g. paper), a plastic material and a textile (woven or non woven). Combinations of these materials may also be used.

Examples of suitable plastic materials include polypropylene, polyethylene, PVC, polycarbonate, polyurethane, nylon, viscose and polyester.

Plastic material may be transparent to allow inspection of the mite growth/maturity directly e.g. by using a stereoscopic microscope without having to take out a sample from the bag. Accordingly, it is preferred that a part of the bag is made of transparent plastic material.

When using e.g. a stereoscopic microscope for the visual inspection through the transparent material, the maturity of the mite culture is generally analyzed as the number of mites per visual field (e.g. number of mites per g).

The bag as such simply has to have enough transparent area to be able to provide an adequate idea of the maturity of the mite culture within the bag. Preferably, the bag comprises at least 10% of transparent area out of the total surface of the bag, more preferred the bag comprises at least 25% of transparent area out of the total surface of the bag and even more preferred the bag comprises at least 50% of transparent area out of the total surface of the bag. A bag that comprises at least 50% of transparent area out of the total surface of the bag is suitably a bag wherein one side is made of transparent plastic material as illustrated in FIG. 3.

Examples of suitable cellulose material include cardboard or more preferably paper.

Non-woven textile is normally made of polymer fibers such as polypropylene or polyethylene fibers. Woven textile could be e.g. cotton.

It is self evident that the bag should be of a material from which the mites within the closed bag should essentially not be able to escape from through the material as such (it may be that some mites do escape from some small holes in the bag but this is not understood as an escape through the material as such).

Generally speaking, a cellulose material (preferably paper) is more oxygen permeable than the majority of herein relevant plastic material. On the other hand plastic material can be transparent.

In a preferred embodiment the bag is made of paper, transparent plastic material and optionally also other suitable materials.

In line of this, a preferred bag is a bag wherein:
1: one side of the bag consists essentially of a cellulose material (preferably paper); and
2: the other side of the bag consists essentially of a transparent plastic material.

An example of such a bag is illustrated in FIG. 3.

The term "consisting essentially of" should be understood as the skilled person would understand it in the present context. The skilled person would understand that, in order to have the significant improvement over the use of flask, the preferred bags as described above does not need to consist 100% of a cellulose material (preferably paper) on one side and 100% of a transparent plastic material on the other side. For instance it may comprise 90% cellulose material (preferably paper) on one side and 90% transparent plastic material on the other side.

The bag as used herein should preferably be of medical grade materials. An example of a suitable medical grade bag is a bag suitable for being used for sterilizing material in an autoclave. Numerous commercial bags are available on the market. The bags suitable for sterilizing material in an autoclave and used in working examples herein are commercially available from Westfield Medical Ltd, UK.

A medical grade bag is generally standardized according to e.g. BS EN ISO 11607-2006 and it must generally fulfill several criteria. For example the porosity must be low enough to avoid crossing of bacteria and microorganisms; it must be sufficiently permeable to vapor, but not to microorganisms; it should be sufficiently resistant to be manipulated and it should essentially be free of toxins that could come into contact with the product. Suitable medical grade bags are usually made of Medical Paper and plastic.

Accordingly, in a preferred embodiment the bag as described herein is medical grade bag, wherein the porosity is low enough to avoid crossing bacteria and microorganisms and thereby also house dust mites; it is sufficiently permeable to vapor, but not to microorganisms and thereby also not to house dust mites; it is sufficiently resistant to be manipulated and it is essentially free of toxins that could come into contact with the mites within the bag.

The size of the bag is in the present context not essential. However for practical reasons it is preferred that the size of the bag is from 20 mm to 2000 mm (broad)×40 mm to 4000 mm (length)×with a possibility to be extended to a suitable height in order for the bag to be able to comprise a relevant amount of the mite culture medium as specified under item (iii) of the first aspect of the invention.

The bag as shown in FIG. 3 and used in the working examples herein is a bag that is 300 mm (broad)×500 (length)×with a possibility to be extended to a height of 65 mm.

In a preferred embodiment the size of the bag is from 50 mm to 1000 mm (broad)×100 mm to 1500 mm (length)×with a possibility to be extended to a suitable height in order for the bag to be able to comprise relevant amount of the mite culture medium as specified under item (iii) of the first aspect of the invention.

Many suitable bags are made of cheap material such as e.g. paper or cheap plastic material. Accordingly, an advantage of using bags as discussed herein is that they may be thrown away after use for the production of the mites, i.e. the bag is not re-used in a subsequent production of mites. An Erlenmeyer flask is quite expensive and must therefore be cleaned after use to be used in a subsequent mite production.

The method of the invention may be used to produce mites in large scale for use in the production of allergen products for use in the diagnosis of allergy and the treatment of allergy by immunotherapy and also to produce mites, e.g. predator mites to be used as biological pest control agents in crops and greenhouses.

House Dust Mites and Storage or Bulb Mites:

In one embodiment of the invention the mite is a house dust mite.

In another embodiment the mite is a storage mite, or a bulb mite.

In a preferred embodiment mite is a mite within the order Acariformes, more preferably within the sub order Astigmata or Prostigmatais.

The method as described herein may be used to produce different mite species at the same time, e.g. an individual bag may comprise different species of mites.

A herein preferred mite, within the order Acariformes, sub order Astigmata and Prostigmata is at least one mite selected from the group consisting of the following families Chortoglyciphidae, Pyroglyphidae, Acaridae and Glyciphagidae. Suitable examples within these families are *Dermatophagoides, Tyrophagus Lepidoglyphus, Glycyphagus, Acarus, Euroglyphus, Blomia, Pyroglyphus, Chortoglyphus* or *Cheyletus*. Some of these mites belong to the group known as house dust mites others are known as storage mites or bulb mites and may be found in house dust.

A herein very preferred mite is a mite selected from the group consisting of the following species: *Dermatophagoides pteronyssinus, Dermatophagoides farinae, Dermatophagoides microceras, Dermatophagoides siboney, Tyrophagus putrescentiae, Lepidoglyphus destructor, Glycyphagus domesticus, Acarus siro, Euroglyphus maynei, Blomia kulagini, Blomia tropicalis* and *Pyroglyphus africanus*

Within the group above, the most preferred house dust mites are *Dermatophagoides pteronyssinus* or *Dermatophagoides farinae*.

Predator Mites

Predatory mites are mites that are predators of pest, in particular crop pests, such as insects, nematodes or arachnids. Typically, predator mites will be useful for control of common crop pests such as trips and whitefly.

Most predatory mites belong to the family Phytoseiidae (order Acarina) and the most common predatory mites in glass houses are *Amblyseius swirskii, Phytoseiulus persimilis, Amblyseius californicus, Amblyseius cucumeris, Amblyseius degenerans* and *Hypoaspis miles*.

Other predatory mites include *Euseius tulalpharensis, Typhlodromus occidentalphalis, Typhlodromus pyri, Zetzellialpha malphali, Amblyseius (Iphiseius) degeneralphans, Amblyseius (Kalphampimodromus) alphaberralphans, Amblyseius (Neoseiulus) balpharkeri, Amblyseius alphandersoni, Amblyseius (Neoseiulus) falphallalphacis, Amblyseius (Euseius) finlalphandicus, Amblyseius (Typhi odromalphalus) lalphailalphae, Amblyseius (Typhlodromalphalus) limonicus, Amblyseius (Typhlodromips) montdorensis, Amblyseius (Euseius) ovalphalis, Amblyseius (Euseius) scutalis, Amblyseius (Euseius) stipulates* and *Amblyseius (Neoseiulus) womersleyi* (also known as *Amblyseius longispinosus*). This list is not exhaustive. McMurtry et al. (Annual Review of Entomology 42, 291-321) categorises the diversity of life-stages in the Phytoseiidae based mainly on food habitats and related biological and morphological traits. As mite taxonomy is continually changing, the number and species of mites classified as predatory mites may change (see for example the Catalogue of Phytoseiidae by Moraes et al. published in 2004 that lists 2,250 species, compared to the previous edition published in 1986 that listed only 1500 species).

The use of these predator mites for pests control are described in more detail in WO 2008/015393.

The present invention may be used to provide a source of predator mites for the control of pest in crops and greenhouses. A particular predator will be selected on the basis of the target pest to be controlled, and the crop to which the predator will be applied.

For example, the predator mites may be used to control one or more of the pests from the following, non-exhaustive list: *Tetranychus* spp. including but not restricted to *Tetranychus urticae, T. cinnabarinus, T. kanzawai, T. turkestani, T. occidentalis; Oligonychus* spp.; *Panonychus ulmi* and *P. citri*; Eriophyid mites including but not restricted to *Aculops lycopersici, Aculus schlectendali, Phyllocoptruta oleivora, Aceriaficus, Rhyncaphytoptus ficifoliae*; Tarsonemid mites including but not restricted to *Polyphagotarsonemus latus, Phytonemus pallidus*; thrips pests including but not restricted to *Frankliniella occidentalis, F. intonsa, F. schultzei, Thrips tabaci, T. palmi, Echinothrips americanus, Heliothrips haemorrhoidalis*; and whitefly pests including but not restricted to *Trialeurodes vaporariorum, Bemisia tabaci, Aleyrodes proletella, A. lonicerae*.

It is preferred to choose a predator mite that will not cause damage to the crop plant itself. The predator mites may be used to control pests on one or more of the crop plants in the following, non-exhaustive list: tomato, sweet pepper, chilli pepper, aubergine, cucumber, beans, squash, melon, strawberry, raspberry, banana, papaya, apple, pear, plum, grape, rose, clirysanthemiim, Gerbera, Begonia, Cyclamen, Poinsettia, Citrus, Skimmia, Choiysia, Daphne and Magnolia.

In one embodiment, the method of the present invention may be used to provide a source of predator mites for the control of thrips (such as *Frankliniella occidentalis* or *Thrips tabaci*) and/or whitefly (such as *Trialeurodes vaporariorum* or *Bemisia tabaci*). In particular, the present invention may be used to provide a source of Amblyseius swirsldi mites for the control of thrips and/or whitefly.

Suitable Solid Growth Medium:

House dust mites and some other mites live naturally in houses such as e.g. in beds. House dust mites feed mainly on human skin scales or squamae.

However, in principle any suitable solid growth medium may be used for mite production in a bag as described herein.

In fact the advantages of using a bag for mite production as described herein may be seen as relative/comparative advantages over the prior art use of a flask or a jar. For such a relative/comparative advantages the medium as such is not so relevant since for making adequate comparative experiments one uses the same medium in both bag and flask.

The prior art describes numerous different media suitable for culturing different herein relevant mites, such as house dust mites. Below is provided a short summary of examples of relevant media.

Mites require area or living space in which to carry out their activities. The area provided by the interior surface of a culture container (e.g. a bag or a flask) is relatively small compared to the area that could be exploited for the container volume. An inert or partially inert substrate can increase the area by orders of magnitude.

A recommended medium for culturing mites usually include 2 ingredients or if only 1 ingredient is included, then portions of the material are inedible.

Virtually all of the media's (diets) that are regularly used contain a significant amount of protein (e.g. from yeast).

There have been numerous studies of the effectiveness of different culture medium ingredients such as: yeast, albumins, feed for animals, feed for fish, shed human skin, skin scales, powdered animal liver, soya flour.

In a preferred embodiment the medium is a medium comprising at least one of the ingredients selected from the group consisting of yeast, albumins, fish derivatives, powdered animal liver, soya flour, hydrolysate of milk proteins, vitamins, minerals, and a protein hydrolysate. The medium preferably comprises two or more of these ingredients.

It may be preferred to use a protein hydrolysate that does not comprise allergens that may cause anaphylactic reactions in sensitized patients.

The medium is preferably heated and dried at 160° C. before it is used. This is normally done before the medium is put into the bag.

For cultivating predator mites as mentioned above the presence of prey mites in the medium is required. The medium may also contain a medium serving as a diet for the prey mites.

The most commonly used prey mites are stored product mites such as *Tyrophagus putrescentiae, Acarus siro* and *Carpoglyphus lactis*.

GB2393890 discloses that *A cucumeris* can be reared using *Tyrophagus putrescentiae, T. tropicus*, or *Acarus siro*. Ramakers et al. (Bulletin-SROP 6(3), 203-206) discloses that rearing of *Amblyseius mckenziei* and *A. cucumeris* can be carried out using wheat bran as the primary food source and *Acarus farris* as substitute prey. Nomikou et al. (Experimental and Applied Acarology 27(1-2), 57-68) discloses that *Tyrophagus putrescentiae* can be used as a food source for *Typhlodromips (Amblyesius) swirsldi*, for obtaining high predator/prey ratios. Steiner et al. (Australian Journal of Entomology 42, 124-130) discloses that *Tyrophagus putrescentiae* can be used as a food source for *Typhlodromips montdorensis*. WO2006/057552 discloses that *Amblyseius swirskii* can be reared on Astigmatid mites, such as mites from the families Carpoglyphidae, Pyroglyphidae, Glyciphagidae or Acaridae. In particular, it discloses that *Carpoglyphus lactis* can be used as a prey mite for rearing *A. swirskii*. The use of various species of stored product mites for raising the predatory mite, *Amblyseius cucumeris*, has also been described Prey mites may be cultivated using a medium comprising at least one on the ingredients selected from the group consisting of yeast, albumins, fish derivatives, powdered animal liver, soya flour, hydrolysate of milk proteins, vitamins, minerals, and a protein hydrolysate. The medium preferably comprises two or more of these ingredients. Some mites need a sugar rich diet. WO 08/015,393 describers preferred diet for prey mites in more detail.

Suitable General Culturing Conditions

The skilled person knows or can routinely identify suitable culturing conditions for a specific mite of interest. In general the culturing conditions described in the art when culturing in a flask or a jar may be used as suitable culturing conditions in a bag as described herein.

Below is provided a summary of suitable mite culturing conditions.

House mites generally grow well at room temperature as might be expected of species that are almost universally present in homes. At general suitable temperature for cultivation of mites is 23° C.±2° C. Temperatures below 10° C. and above 35° C. are generally not suitable for the majority of relevant mites. A herein preferred suitable temperature may be 23° C.±5° C.

The humidity of the air is an important factor. A number of relevant mites (e.g. *D. farinae*) is capable of extracting water from the air if the relative humidity (RH) is above 70%. Too high humidity is generally not suitable because culture medium that is not 100% sterile will be destroyed if the humidity is high enough to foster significantly bacterial or fungal growth.

In general one may say that a suitable humidity could from 70 to 85% RH.

A suitable period of culturing will depend on the specific mite of interest. Depending on the species, the development from egg through larva, protonymph, tritonymph to adult mite may require around a month in suitable cultures.

The prior art describes that for some culture conditions optimal mite protein content in the mite culture (for allergen extraction) is achieved after 5-16 weeks e.g. for *D. Dermatophagoides.*

Generally speaking and for many herein relevant mites reared undersuitable culturing conditions the culturing period is from 1 to 24 weeks, normally from 4 to 20 weeks.

Characteristic of the Bag during the Culturing

During the mite culturing process, the culture medium comprising the growing/cultured mites is present as a relatively thin layer within the bag to give a relatively big surface.

In a preferred embodiment the culture medium comprising the growing/cultured mites is present as a relatively thin layer within the bag to give a relatively large surface, defined as aculture layer that is less than 90 mm in height, more preferred less than 70 mm in height, even more preferredless than 60 mm in height and most less than 55 mm in height.

In a very preferred embodiment the culture layer is from 10 mm to 50 mm in height.

During the mite culturing process the closed bag comprises at least 25 g medium. As discussed above, one advantage of using bags in the production of mites relates to the possibility of making a more efficient industrial mite production.

Accordingly, in a preferred embodiment the closed bag comprises at least 100 g medium, more preferred at least 400 g medium, even more preferred at least 750 g medium and most preferred at least 1000 g medium.

As discussed above, the better and more uniform oxygen supply in the bags allow efficient growth of the mites in bags with a relatively little open space around the medium in the bags. This provides the possibility to have more bags (i.e. more medium) in a production room, as compared to the use of flasks, and therefore much more mites can be produced within the same production room.

Compared to a flask or jar a bag is more flexible and may therefore relatively easy change shape (e.g. be folded). In the present context a bag may e.g. be shaped (e.g. folded) around the mite culture medium in order to contain the medium within the bag with a relatively little free open space around the medium within the bag (see e.g. FIG. 3 herein).

In a preferred embodiment there is during the culturing of the dust mites relatively little free space within the closed bag, meaning that the culture medium occupies at least 30% of the total volume of the closed bag with medium as the closed bag with medium is physically present in the production room during the culturing of the dust mites. More preferred, the culture medium occupies at least 50% of the total volume of the closed bag with medium, even more preferred the culture medium occupies at least 70% of the total volume of the closed bag with medium and most preferred the culture medium occupies at least 80% of the total volume of the closed bag with medium as the closed bag with medium is physically present in the production room during the culturing of the dust mites.

The term "as the closed bag with medium is physically present in the production room" should be understood as the skilled person would understand it in the present context. For instance, in an open bag as illustrated in FIG. 5 there is more free space than in a closed bag as illustrated in FIG. 3. As understood by the skilled person in the present context, an open bag as illustrated in FIG. 5 is not a closed bag as it is physically present in the production room.

Use of a Number of Bags for Mite Culturing

As discussed above, the bags as described herein can relatively easy be piled in e.g. a rack as shown in FIG. 4 and consequently it is possible to have numerous piled bags in a industrial relevant production room (see e.g. FIG. 4). The end result is that the use of the bags significantly increases the production capacity in a room (can have more mite medium and thereby mites) as compared to use of flasks.

Accordingly, in a preferred embodiment the production room comprises at least 10 bags, more preferred at least 50 bags, even more preferred at least 1000 bags and most preferred at least 10000 bags.

For practical reasons it is difficult to imagine that a production room can be so large that it can comprise more than 1.000.000 bags.

The bags may be piled on top of each other in a suitable rack system where the top surface of a lower bag is not touching the bottom surface of an upper bag.

In line of above it is preferred that the bags are piled in a suitable rack system as illustrated in FIG. 4.

In a preferred embodiment the production room comprises a suitable rack system with at least 2 bags piled on top of each other, more preferred with at least 5 bags piled on top of each other and even more preferred the production room comprises a suitable rack system with at least 8 bags piled on top of each other.

An advantage of having the bags piled on top of each other is that a common/single container at the bottom of the rack is sufficient to trap mites that may escape from the bags. An example of this is shown in FIG. 4, where the trapping container is a metal tray. The trapping container may advantageously comprise a trapping material such as e.g. paraffin or lanolin.

When flasks are used such a trapping container has to be placed around each individual flask since flasks are not easily piled on top of each other.

Accordingly, in a preferred embodiment the suitable rack system with at least 2, 5 or 8 bags piled on top of each other comprises a common/single container at the bottom of the rack to trap mites that may escape from a bag. An example of such a trapping container is a tray such as e.g. a metal or a plastic tray. In a preferred embodiment the trapping container comprises a trapping material such as e.g. paraffin or lanolin.

In a preferred embodiment the production room comprises at least 2 suitable rack systems as described above, more preferred at least 10 suitable rack systems as described above, even more preferred at least 20 suitable rack systems as described above and most preferred at least 100 suitable rack systems as described above.

For practical reasons it is difficult to imagine that a production room can be so large that it can comprise more than 200.000 suitable rack systems as described above.

Isolation/Extraction of Mite Allergens

A main purpose of industrial relevant mite mass production is to isolate/extract mite allergens to prepare allergenic extracts used in allergy formulations to be used, for example, in in vivo or in vitro allergy tests, or in desensitizing preparations given to patients.

The extraction may be made on the whole culture, where allergens from both the mites and mite fecal particles are obtained. It is known that mite fecal particles are an important source of house dust mite allergens.

The mites may be separated from the culture medium and/or fecal particles by means of physical methods such as sieving or flotation in various solutions.

The allergenic raw material generally undergoes a process of extraction in aqueous solution (e.g. saline solution, phosphate buffer saline solution, ammonium bicarbonate solution 0.05-0.125 mol/L, etc.) with stirring, at a pH of 5-9. In this way the allergenic proteins are dissolved in the supernatant, whereas most of the components of the culture do not dissolve.

The supernatant is recovered (e.g. after centrifugation) and the allergens with an appropriate kDa size (normally bigger than 5 kDa) is isolated. Said in other words "impurities" of low molecular weight (generally below 5 kDa) are removed by e.g. dialysis over a membrane with a 5 kD cut-off, ultrafiltration or molecular sieve chromatography.

The allergenic activity of the isolated allergens may be determined by a number of known methods such as e.g. ELISA or Rast inhibition.

Finally, the mite allergen product is formulated with the addition of e.g. suitable excipients and then it may undergo sterile filtration and lyophilization. The extract typically contains from 5-60% of Group 1 allergens (relative to the total content of proteins) and it typically also contains allergens of Group 2, 3 and others in lower proportions. Apart from the lyophilized allergenic extract, a suitable final pharmaceutical composition may contain relevant pharmaceutical excipients. The pharmaceutical composition may e.g. be an injectable solution or a composition for oral administration.

Of course one may further purify the mite allergen extract to get more pure samples containing e.g. purified relevant Group 1 allergens such as the allergens Der p1 (*Dermatophagoides pteronyssinus*), Der f1 (*D. farinae*), Eur m1 (*Euroglyphus maynei*), Der s1 (*D. siboney*).

In one embodiment the invention relates to the method, as described herein, wherein the method is followed by suitable subsequent steps in order to isolate a suitable mite allergen composition that are subsequently incorporated into a suitable pharmaceutical composition.

EXAMPLES

Example 1

Mite Culturing in Bags

Materials:
Mite species: *D. farinae*
Medium: The medium was a standard mite culturing medium comprising essentially protein hydrolysates, yeast, vitamins and minerals.
Bag: A bag for sterilization of materials in an autoclave where one side is made of oxygen permeable paper material and the other side is made of transparent plastic material. The size of the bag is 300 mm (broad)×500 (length)×with a possibility to be extended to a height of 65 mm. The bag is commercially available from Westfield Medical Ltd, UK.
Culturing Method:
500 g of medium was put in each bag (illustrated in FIG. 5). The medium was seeded with a sample of conventional seed cultures of *D. farinae* and the bag was thereafter sealed/closed (a closed bag is illustrated in FIG. 3).

Cultivation took place in a production room at a temperature of 23° C. (±2°) at a relative humidity (RH) of 80% (±5%).

Using a stereoscopic microscope the maturity of the mite culture was inspected by visual inspection through the transparent plastic material.

When the maturity was considered optimal the culture was harvested.

The culture was used to obtain allergens from the mite bodies and faeces. The two fractions (faeces and bodies) were separated by sieving.

In preparing extracts of the two fractions (faeces and bodies), the allergenic raw material was extracted in saline solution with a homogenizer (Ultraurrax) for 10-20 minutes at 6° C. In this way the allergenic proteins were dissolved in the supernatant.

The supernatant was recovered after centrifugation at 3000 rpm for 15 minutes at 4° C. The allergens with kDa size bigger than 5 kDa were isolated by ultrafiltration.

The total allergenic activity of the isolated allergens was analyzed by Rast inhibition. The specific allergenic activity was measured by ELISA.

The results of the allergenic activity analysis in the body fraction were 2700 μg/g Der f 1.

In this example culture and medium from 200 bags was used, which means that 200×500 g=100 kg was cultured. After sieving 3710 g mite culture (mites and feaces) was obtained. The total quantity of Der f 1 obtained is 2700 μg×3710 g=10.017 g of purified allergen form 200 bags. Accordingly, the allergenic activity per gram of purified medium was 2700 μg/g but the total quantity of allergen with 200 bags was 10.017 g.

Example 2

Mite Culturing in Flask—for Comparison

Flask: 250 ml Erlenmeyer flask that comprised 30 g medium and was closed with a cotton plug.

All the mite culturing conditions was identical to the conditions used in bag example 1. The same growth medium, the same growth conditions, the same period of time and the same production room was used.

The maturity of the mite culture was inspected and when the maturity was considered optimal the culture was harvested.

The extraction and isolation of allergens were done as in Example 1.

The allergenic activity was analyzed as in Example 1.

The results of the allergenic activity analysis were 2563 µg/g Der f 1.

In this example medium from 600 flasks was used, which means that 600×30 g=18 kg was used for culturing mites. After sieving 710 g was obtained. The total quantity of Der f 1 obtained was 2563 µg×710 g=1.82 g of purified allergen from 600 flasks.

Accordingly, the allergenic activity per gram of purified medium was 2563 µg/g but the total quantity of allergen with 600 flasks was 1.82 g.

Conclusions Derivable from Example 1 (bags) and Example 2 (flask)

The allergenic activity per gram medium was the same for mite production in bags (example 1) as for production in Erlenmeyer flasks (example 2).

As discussed herein and illustrated in the examples the use of bags, as compared to the use of flasks, makes it possible to have much more mite medium within the same production room and thereby the total mite allergen production per physical production room is much higher when bags as described herein are used as compared to the use of flasks.

References

1: EP1236394B1 (Stallergenes—family with US2003/0059445A1)
2: T. Batard et al (Int Arch Allergy Immunol 2006; 140:295-305)
3: F. C. Yi et al (Asian Pacific J. of Allergy and Immunology (1999) 17: 189-194)
4: J. Miyamoto (Japan, J. Exp. Med. Vol, 45, 2. p. 133-138, 1975)
5: J. Med. Ent. Vol 12, no. 6: 577-621, 1976)
6. Ivanov and Petrova describes in Medisinskaja Parazitoligija i Parazitarnye Bolezni, 46-49, 1985
7. Crop Protection, 5(2): 122-124, 1986

The invention claimed is:

1. A method for culturing and producing mites for preparation of allergenic extracts used in allergy formulations, comprising: a) adding a suitable solid culture medium to a closed bag; b) seeding the suitable solid culture medium with mites; c) piling multiple closed bags on top of each other in a suitable rack system where top surface of a lower closed bag is not touching bottom surface of an upper closed bag; d) culturing the mites in the suitable solid culture medium, under suitable conditions and for a suitable period of time in a suitable production room, wherein the mites are at least one mite selected from the group consisting of the following species: *Dermatophagoides pteronyssinus, Dermatophagoides farinae, Dermatophagoides microceras, Dermatophagoides siboney, Tyrophagus putrescentiae, Lepidoglyphus destructor, Glycyphagus domesticus, Acarus siro, Euroglyphus maynei, Blomia kulagini, Blomia tropicalis* and *Pyroglyphus africanus* and e) obtaining allergens from the cultured mites; wherein:

i: the closed bag has an oxygen permeability that is sufficient to allow growth of the mites;
ii: the closed bag comprises an area which is transparent to allow inspection of the mites growth;
iii: the culture medium comprising the growing/cultured mites is present as a layer of less than 110 mm in height; and
iv: the closed bag comprises at least 25 g of the culture medium, and further wherein the closed bag is an oxygen permeable bag having an air permeability of at least 150 ml/min as measured according to the standard ISO 5636-3, Bendtsen method; or further wherein the closed bag has an oxygen permeability of at least 10 $cm^3$ oxygen per closed bag per day measured according to a standard test method of American Standards National Institute document/standard ASTM F1307-02 for oxygen transmission rate through dry packages using a coulometric sensor; or further wherein the closed bag has an oxygen permeability that is sufficient to provide at least the same yield of mites per gram of the culture medium in the closed bag as the yield of mites in a 250 ml Erlenmeyer flask that comprises 30 g of the culture medium and is closed with a cotton plug, wherein the closed bag and the Erlenmeyer flask are cultured under identical conditions.

2. The method of claim 1, wherein the culture medium occupies at least 70% of the total volume of the closed bag with the culture medium in the closed bag, when the culture medium is physically present in the production room during the culturing of the dust mites.

3. The method of claim 1, wherein the closed bag is made of at least one material selected from the group of materials consisting of a cellulose material, a plastic material, a woven or non woven textile; and wherein the closed bag is made of a material which substantially prevents the mites within the closed bag from escaping through the material.

4. The method of claim 3, wherein:
a) one side of the closed bag consists essentially of a cellulose material; and
b) the other side of the closed bag consists essentially of a transparent plastic material.

5. The method of claim 3, wherein the size of the closed bag is from 50 mm to 1000 mm (width) ×100 mm to 1500 mm (length) with a possibility to be extended to a suitable height in order for the closed bag to be able to include the culture medium comprising the growing/cultured mites present as a layer of less than 110 mm in height; and wherein the closed bag comprises at least 400 g of the culture medium.

6. The method of claim 1, wherein the mite culturing conditions are:
a) the temperature is 23° C. ±5° C.;
b) the humidity is from 70 to 85% relative humidity (RH);
c) the culturing period is from 1 to 24 weeks.

7. The method of claim 1, wherein the culture medium comprising the growing/cultured mites is present as a layer of less than 60 mm in height.

8. The method of claim 1, wherein the production room comprises at least 50 closed bags.

9. The method of claim 8, wherein the production room comprises at least 10 suitable rack systems, wherein each rack system is a rack system with at least 5 closed bags piled on top of each other.

10. The method of claim 9, wherein each rack system is a rack that comprises a trapping container at the bottom of a rack to trap mites that may escape from the closed bag.

11. The method of claim 10, wherein the trapping container is a tray; and wherein the trapping container comprises a trapping material.

12. The method of claim 1, wherein the method is followed by suitable subsequent steps to isolate a suitable mite allergen composition that is subsequently incorporated into a suitable pharmaceutical composition.

13. The method of claim 3, wherein the cellulose material is paper.

14. The method of claim 4, wherein the cellulose material is paper.

15. The method of claim 1, wherein the tray is a metal tray.

16. The method of claim 11, wherein the trapping material is paraffin or lanolin.

17. The method of claim 1, wherein the closed bag is a bag suitable for sterilizing material in an autoclave.

18. The method of claim 1, wherein the closed bag is a medical grade bag, whose porosity is low enough to avoid crossing bacteria and microorganisms.

19. The method of claim 6, wherein the culturing period is from 4 to 20 weeks.

20. The method of claim 1, wherein the closed bag comprises at least 500 g of the culture medium.

* * * * *